United States Patent [19]

Wu

[11] Patent Number: 4,803,160

[45] Date of Patent: Feb. 7, 1989

[54] USE OF POLYMERIC MORDANTS TO INCREASE THE INTENSITY OF RIGID FLUORESCENT DYES

[75] Inventor: Annie L. Wu, Penfield, N.Y.

[73] Assignee: Eastman Kodak Company, Rochester, N.Y.

[21] Appl. No.: 824,755

[22] Filed: Jan. 31, 1986

[51] Int. Cl.[4] ............................................. C12Q 1/02
[52] U.S. Cl. ........................................ 435/29; 435/4; 435/7; 436/546; 436/800; 436/805; 424/3
[58] Field of Search ................ 436/800; 424/3; 435/7, 435/29, 4

[56] References Cited

U.S. PATENT DOCUMENTS

| | | |
|---|---|---|
| 3,936,357 | 2/1976 | Milligan et al. . |
| 4,069,017 | 1/1978 | Wu et al. . |
| 4,204,839 | 5/1986 | Wu et al. . |
| 4,283,382 | 8/1981 | Frank et al. ......................... 436/800 |
| 4,338,095 | 7/1982 | Wu . |

OTHER PUBLICATIONS

O'Brien et al., *Photo. Sci. Eng.*, 18 (1); pp. 76–84 (1974).
Tan et al., *J. Phys. Chem.*, 79 (14), pp. 1380–1386 (1975).
Kamat et al., *J. Phys. Chem.* 88 (11), pp. 2297–2302 (1984).

*Primary Examiner*—Sam Rosen
*Attorney, Agent, or Firm*—J. Lanny Tucker

[57] ABSTRACT

Polymeric mordants are used with certain rigid fluorescent dyes or precursors thereof to increase fluorescence intensity. Compositions and analytical elements containing the mordants and dyes or dye precursors are useful in biological studies, such as cell and tissue staining and cell cytometry, and in analytical determinations for various analytes, e.g. living organisms.

24 Claims, 1 Drawing Sheet

FIG. 1 though, with and without the polymeric mordant of this invention.

USE OF POLYMERIC MORDANTS TO INCREASE THE INTENSITY OF RIGID FLUORESCENT DYES

CROSS-REFERENCE TO RELATED APPLICATIONS

Reference is made to the following copending and commonly assigned applications:

U.S. Ser. No. 824,766, filed on even date herewith by Belly et al and entitled REDUCIBLE COMPOUNDS AND ANALYTICAL COMPOSITIONS, ELEMENTS AND METHODS UTILIZING SAME which is a continuation-in-part of U.S. Ser. No. 699,386 filed Feb. 7, 1985.

U.S. Ser. No. 824,757, filed on even date herewith by Babb et al and entitled BIOLOGICAL AND ANALYTICAL USES OF PHENALENONE AND BENZPHENALENONE COMPOUNDS, and U.S. Ser. No. 824,756, filed on even date herewith by Babb et al and entitled HYROLYZABLE FLUORESCENT SUBSTRATES AND ANALYTICAL DETERMINATIONS USING SAME.

U.S. Ser. No. 824,752, filed on even date herewith by Sundberg et al and entitled HYDROLYZABLE FLUORESCENT SUBSTRATES FOR PHOSPHATASES AND ANALYTICAL USE THEREOF.

FIELD OF THE INVENTION

This invention relates to compositions and elements comprising polymeric mordants and rigid fluorescent dyes or fluorescent dye precursors. It also relates to the use of such material for biological studies or analytical determinations. In particular, it relates to clinical chemistry.

BACKGROUND OF THE INVENTION

The staining of biological cells and tissues with dyes, especially fluorescent dyes, in order to render them more observable or to differentiate types of cells, is well known in the art. There is a continuing need to find more efficient means of staining.

Further, chemical analysis of liquids, such as water, milk and biological fluids is often desirable or necessary for health maintenance and diagnostic care. Various compositions and elements to facilitate such analyses are known. Such compositions and elements generally include a reagent composition for determining a substance under analysis, identified as an "analyte" herein. The analyte can be a living organism, such as a bacterium or a yeast cell, or a nonliving chemical substance. The reagent composition, upon interaction with the analyte, provides a detectable change (e.g. dye formation).

Recently, much work has been directed to developing compositions and elements which are useful for rapid and highly quantitative diagnostic or clinical analysis of biological fluids such as whole blood, blood sera, plasma, urine and the like.

For example, for the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. Most urinary tract infections are associated with bacterial counts of 100,000 or more organisms per ml of urine, a condition referred to as significant bacteriuria.

In U.S. Ser. No. 824,766 of Belly et al noted above, novel reducible compounds are described and claimed which are useful in the detection of bacteria as well as other analytes. The compounds and assays described in this application can be used to determine an analyte, e.g. a bacterium, which reduces a reducible compound thereby releasing a detectable species, e.g. a colored or fluorescent dye, at a pH of 9 or less.

In U.S. Ser. No. 824,757 of Babb et al noted above, certain reducible compounds are described which are useful for releasing phenalenone and benzphenalenone fluorescent dyes. These dyes can be used to stain biological specimens and to determine an analyte, such as a bacterium.

While those assays represent significant advances in the art, it would be desirable to improve the sensitivity of the assays even further in order to extend their usefulness to determine analytes at much lower concentrations.

SUMMARY OF THE INVENTION

The present invention provides a means for significantly increasing fluorescent intensity using a composition which comprises a rigid phenalenone, benzphenalenone or 4-oxo-4H-benz-[d,e]anthracene fluorescent dye or precursor thereof and a cationic or nonionic polymeric mordant. This composition can be used for distinguishing cells by contacting a biological sample with the composition.

Further, this invention provides a dry analytical element for the determination of an analyte comprising an absorbent carrier material and containing, in association, the rigid fluorescent dye or precursor thereof described above and a cationic or nonionic polymeric mordant.

Still further, a method for the determination of an analyte comprises the steps of:

A. contacting a sample of a liquid suspected of containing an analyte with a fluorescent dye precursor which releases a rigid phenalenone, benzphenalenone or 4-oxo-4H-benz-[d,e]anthracene fluorescent dye in the presence of the analyte, and     a cationic or nonionic polymeric mordant, and B. determining the fluorescent dye released as a result of the presence of the analyte.

This invention also provides a method for staining a biological specimen comprising contacting the specimen with the composition described above.

The advantages of this invention are obtained by using a cationic or nonionic polymeric mordant with a particular rigid fluorescent dye or dye precursor thereof. While it is known that fluorescence of a nonplanar or nonrigid compound can be enhanced by making it more rigid, e.g. with a mordant, it is unexpected that a mordant can intensify the fluorescence of phenalenone, benzphenalenone and 4-oxo-4H-benz-[d,e]anthracene compounds which are already rigid.

This invention can also be used to advantage to significantly increase the fluorescent intensity of these rigid fluorescent dyes in biological studies, such as staining biological specimens, e.g. cells and tissues and in cell cytometry.

BRIEF DESCRIPTION OF THE DRAWING

The FIGURE contains graphical plots of the change in fluorescence over time for a composition of this invention and a Control composition. This FIGURE is discussed in more detail in Example 4 below.

DETAILED DESCRIPTION OF THE INVENTION

The fluorescent dyes useful in the practice of the present invention include any rigid substituted or unsubstituted phenalenone, substituted or unsubstituted benzphenalenone or substituted or unsubstituted 4-oxo-4H-benz-[d,e]anthracene which, when excited at a particular wavelength, fluoresce or emit detectable radiation at another wavelength. As used in this application, the term "rigid" refers to compounds having two or more fused rings and which are therefore fixed-in-space in a restricted number of configurations. The useful substituted or unsubstituted anthracenes are described in copending and commonly assigned U.S. Ser. No. 824,765 filed on even date herewith by Goswami et al and entitled FLUORESCENT DYES AND BIOLOGICAL AND ANALYTICAL USES THEREOF.

The substituted or unsubstituted phenalenones and benzphenalenones described in U.S. Ser. No. 824,757 of Babb et al noted above are preferred in the practice of this invention. These compounds have the following structures:

wherein R is hydroxy, mercapto or amino [HN(R')—]. R' is hydrogen, substituted or unsubstituted alkyl (preferably of 1 to 10 carbon atoms, e.g. methyl, ethyl, isopropyl, decyl, benzyl, etc.), substituted or unsubstituted cycloalkyl (preferably of 5 to 12 carbon atoms, e.g. cyclopentyl, cyclohexyl, etc.), substituted or unsubstituted phenyl or a substituted or unsubstituted heterocyclic group, e.g. pyridyl or thienyl. Preferably, R' is hydrogen or substituted or unsubstituted alkyl of 1 to 3 carbon atoms. The compounds can have one or more other substituents on any of the fused rings as long as the fluorescence is not adversely affected. Such substituents include substituted or unsubstituted alkyl (preferably of 1 to 12 carbon atoms, e.g. methyl, ethyl, benzyl, etc.), substituted or unsubstituted hydroxyalkyl (preferably of 1 to 12 carbon atoms, e.g. hydroxymethyl, 2-hydroxyethyl, etc.), substituted or unsubstituted alkoxycarbonyl (preferably of 2 to 12 carbon atoms, e.g. methoxycarbonyl, ethoxycarbonyl, etc.), halo (e.g. fluoro, chloro, bromo), cyano, carboxy, acyl, substituted or unsubstituted arylsulfonyl (preferably of 6 to 10 carbon atoms, e.g. phenylsulfonyl, tolylsulfonyl, etc.), substituted or unsubstituted alkylsulfonyl (preferably of 1 to 6 carbon atoms, e.g. methylsulfonyl, ethylsulfonyl, etc.), and other substituents known to one skilled in the art.

Representative phenalenone and benzphenalenone fluorescent compounds include:

I

II

III and

IV with compounds I and II being particularly useful. Methods for preparing these compounds are described in the noted Babb et al application.

The rigid fluorescent dyes can also be derived from a dye precursor which can be subjected to some treatment or condition which will release the rigid fluorescent dye during the assay. For example, the dye precursor can be hydrolyzed chemically or enzymatically by an analyte or other reagents used in the assay. In one embodiment, dye precursors which are substrates for hydrolases, such as esterases (e.g. diacetinase) and amidases (e.g. aminoacylase) can be used in the practice of this invention.

The substrates have the following structures:

wherein X is oxy, thio or imino [—N(R'')—, wherein R'' is defined the same as R' above, i.e. hydrogen, substituted or unsubstituted alkyl, substituted or unsubstituted cycloalkyl, substituted or unsubstituted phenyl or a substituted or unsubstituted heterocyclic group, such as pyridyl or thienyl], SUB represents one or more substituents as defined above for the phenalenone and benzphenalenone compounds, and BLOCK is a blocking group, such as acyl, phosphono, thioxophosphono or a moiety derived from an amino acid, peptide or mono- or polysaccharide which can be cleaved from the remainder of the molecule by hydrolysis.

Preferred substrates include:

Such dye precursors and their use as enzyme substrates are described in more detail in U.S. Ser. No. 824,756, of Babb et al noted above.

In another embodiment, the dye precursor has the structure CAR($-R^1)_n$ wherein CAR— is a substituted or unsubstituted aromatic or quinone nucleus, $R^1$ comprises a substituted or unsubstituted phenalenone or benzphenalenone moiety derived from the compounds described above and n is 1 or 2. This precursor is capable of being reduced at a pH of 9 or less. When $R^1$ is replaced with H, CAR($-H)_n$ has an $E_{\frac{1}{2}}$ of either at least about $+100$ mV when measured in water. This $E_{\frac{1}{2}}$ value facilitates the reduction and subsequent release of $R^1$ from CAR— at physiological pH (i.e. pH of 9 or less) in the determinations of biological analytes. Such measurements are made according to standard electrochemical techniques using either differential pulse polarography or cyclic voltametry (see e.g. Sawyer and Robert, Jr., *Experimental Electrochemistry for Chemists,* John Wiley & Sons, New York, 1972). Preferably, the $E_{\frac{1}{2}}$ is from about $+100$ mV to about $+400$ mV as measured in water.

Such fluorescent dye precursors are described in considerable detail in U.S. Ser. Nos. 824,766 and 824,757 of Belly et al and Babb et al noted above, respectively. Such precursors are "shifted", i.e. the spectra of the released dyes are different than the spectra of the dye precursors.

In a preferred embodiment, the reducible fluorescent dye precursors useful in this invention are RIND compounds, i.e. reducible compounds capable of undergoing intramolecular nucleophilic displacement at physiological pH to release one or more rigid fluorescent dyes when a nucleophilic group is generated by at least a one electron reduction of the compound. In other words, such displacement occurs when the RIND compound is reduced by a suitable reductant.

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds useful in this invention have the nucleophilic and electrophilic groups juxtaposed in the three-dimensional configuration of the molecule in close proximity whereby the intramolecular reaction can take place and a ring is formed having from 4 to 7 atoms, and preferably having 5 or 6 atoms.

Particularly useful RIND compounds are those which have the structure CAR—$R^1$ wherein CAR— is $R^1$ is wherein m is 0 or 1, and preferably 1. $R^5$ is substituted or unsubstituted alkylene, preferably of 1 or 2 carbon atoms in the backbone (e.g. methylene, ethylene, alkoxymethylene, etc.). Most preferably, $R^5$ is methylene. Q is carbonyl or thiocarbonyl and preferably carbonyl. $R^6$ is methyl.

FRAG is a shiftable fluorescent dye as defined above. That is, it has first spectral absorption and emission bands when attached to the RIND compound, and second spectral absorption and emission bands when released as a rigid fluorescent dye. This dye is released in an amount which can be directly related to the amount of reductant (i.e. analyte) present.

FRAG is linked to Q by means of a single bond through a bivalent monoatom linkage which is a part of FRAG. Preferably, the monoatom linkage is oxy or thio, and most preferably it is oxy.

$R^2$, $R^3$ and $R^4$ in the above quinone structure are independently hydrogen, substituted or unsubstituted alkyl of 1 to 40 carbon atoms (e.g. methyl, ethyl, hydroxymethyl, methoxymethyl, benzyl, etc.) substituted or unsubstituted aryl (e.g. phenyl, naphthyl, methylnaphthyl, p-nitrophenyl, m-methoxyphenyl, phenylsulfonamido, etc.) or an electron withdrawing group which generally has a positive Hammett sigma value, and preferably has a sigma value greater than about 0.06. Hammett sigma values are calculated in accordance with standard procedures, e.g. described in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (e.g. fluoro, bromo, chloro, iodo), trihalomethyl (e.g. trifluoromethyl, trichloromethyl, etc.), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of fluorescent dye molecules to original RIND compound molecules.

Alternatively, $R^3$ and $R^4$, taken together, can represent the carbon atoms necessary to complete a substituted or unsubstituted fused carbocyclic ring attached to the quinone nucleus. For example, such a ring (mono- or bicyclic) can have from 4 to 8, and preferably from 5 to 7, carbon atoms in the backbone.

Representative preferred RIND dye precursors are listed in Taable I below in reference to the following structure:

The $E_{\frac{1}{2}}$ values of Table I were measured in an aqueous emulsion of the quinone dissolved in N,N-dimethylformamide, a nonionic surfactant (TRITON X-100) and sodium phosphate buffer (pH 7). A normal hydrogen electrode was used as a standard.

TABLE I

| RIND Compound | $R^6$ | $R^2$ | $R^4$ $R^3$ | FRAG | $E_{\frac{1}{2}}(mV)$ |
|---|---|---|---|---|---|
| I. | —$CH_3$ | phenyl with —CN | $R^3$ and $R^4$ together form (bicyclic ring) | —O—(naphthyl ketone) | +220 |
| II. | —$CH_3$ | phenyl | $R^3$ and $R^4$ together form (cyclopentyl ring) | —O—(naphthyl ketone) | +222 |
| III. | —$CH_3$ | phenyl with Cl, Cl | $R^3$ and $R^4$ together form (cyclopentyl ring) | —O—(naphthyl ketone) | +236 |
| IV. | —$CH_3$ | phenyl with $NO_2$ | $R^3$ and $R^4$ together form (bicyclic ring) | —O—(naphthyl ketone) | +214 |

TABLE I-continued

| RIND Compound | $R^6$ | $R^2$ | $R^4$ $R^3$ | FRAG | $E_{\frac{1}{2}}(mV)$ |
|---|---|---|---|---|---|
| V. | —$CH_3$ | —⟨⟩—$NO_2$ | $R^3$ and $R^4$ together form | —O—(naphthalenone) | +236 |
| VI. | —$CH_3$ | —⟨⟩—$SO_2NH(CH_3)_2$ | $R^3$ and $R^4$ together form | —O—(naphthalenone) | +212 |

The RIND dye precursors useful in this invention are prepared using a sequence of individually known reactions. Generally, the preparation sequence includes the following general steps: (1) preparation of the substituted hydroquinone, (2) oxazine ring formation, (3) oxazine ring opening, (4) preparation of the carbamoyl chloride, and (5) reaction of the FRAG moiety with the carbamoyl chloride. Representative preparations are provided in the Belly et al and Babb et al applications noted above.

Other useful RIND compounds include those having the appropriate $E_{\frac{1}{2}}$ values and the structure CAR$(-R^1)_n$ wherein:

(1) CAR— is a substituted or unsubstituted nucleus of a 1,2-naphthoquinone, 1,2-, 1,4- or 9,10-anthraquinone, 4,4'-diphenoquinone, azuloquinone or 1,6-[10]-anulenoquinone wherein $R^1$ is attached to the nucleus one carbon atom distant or in the peri position from one of the oxo groups of the nucleus. The nucleus can be substituted with one or more electron withdrawing groups as described above for $R^2$ or have one or more fused rings as described above for $R^3$ and $R^4$.

$R^1$ is as defined above, and n is an integer of 1 or 2.

(2) CAR— is

-continued any of which can be substituted with one or more electron withdrawing groups as described above for $R^2$, $R^3$ and $R^4$. $R^1$ is as defined above, and n is 1 or 2.

(3) CAR— is a substituted or unsubstituted nitrobenzenoid nucleus of the structure wherein $R^7$ is substituted or unsubstituted alkyl of 1 to 20 carbon atoms (e.g. methyl, ethyl, methoxymethyl, isopropyl, dodecyl, hexadecyl, octadecyl, etc.), and $R^1$ is as defined above and n is 1.

All of these reducible compounds can be prepared using techniques and starting materials known in the art or readily apparent to a skilled synthetic chemist.

One or more of the fluorescent dyes or dye precursors described herein are used in combination with one or more cationic or monionic polymeric mordants. Such materials are well known in the art, e.g. U.S. Pat. Nos. 3,958,995 (issued May 25, 1976 to Campbell et al), 4,069,017 (issued Jan. 17, 1978 to Wu et al), 4,124,386 (issued Nov. 7, 1978 to Yoshida et al), and 4,247,615 (issued Jan. 27, 1981 to McGuckin et al) and *Research Disclosure Publication* 12045 (April, 1974), available from Kenneth Mason Publications, Ltd., The Old Harbourmaster's, 8 North St., Emsworth, Hampshire, P010 7DD, England. The cationic mordants contain one or more charge-bearing cationic groups (e.g. cationic quaternary ammonium or phosphonium groups), while the nonionic mordants contain no charged groups.

Representative mordants useful in the practice of this invention include:
poly(N,N,N-trimethyl-N-vinylbenzylammonium chloride)
poly[styrene-co-N-benzyl-N,N-dimethyl-N-(p-vinylbenzyl)ammonium chloride],
poly(N,N,N-trioctyl-N-vinylbenzylphosphonium chloride)
poly[styrene-co-N-vinylbenzyl-N,N,N-trihexylammonium chloride]
poly(styrene-co-N,N,N-trimethyl-N-vinylbenzylammonium chloride),
poly(styrene-co-N,N-dimethyl-N-(p-vinylbenzyl)ammonium chloride-co-divinylbenzene),
poly[1-vinylimidazole-co-3-(2-hydroxyethyl)-1-vinylimidazolium chloride],
poly[N-benzyl-N,N-dimethyl-N-(p-vinylbenzyl)ammonium chloride],
poly(vinylpyrrolidone),
poly[acrylonitrile-co-1-vinylimidazole-co-3-(2-hydroxyethyl)-1-vinylimidazolium chloride], and
poly(N-cyclohexyl-N,N-dimethyl-N-vinylbenzylammonium chloride).

Each mordant may affect different rigid fluorescent dyes to a different degree. For example, some dyes may not be enhanced by every mordant. Some mordants may enhance the intensity of some dyes, but not others. It has been found, however, that each mordant unexpectedly increased the intensity of these particular rigid fluorescent dyes.

The mordants can be prepared using techniques and starting materials known to one skilled in the art. Some of them are commercially available.

The rigid fluorescent dyes and mordants described herein are generally more soluble in water than the dye precursors. Therefore, the compositions of dyes and mordants can generally be prepared using an aqueous or buffer solution. In some instances, a water-miscible solvent or the combination of such a solvent and a surfactant may be needed to dissolve a given dye. The dye precursors have generally limited water solubility and must be dissolved in a solution or dispersion including either a water-miscible solvent or a surfactant or both.

Surfactants which are useful in the practice of this invention include any surfactants which do not inhibit analyte determination. Generally, for determination of living cells, the useful surfactants are nonionic surfactants including, for example, alkylarylpolyethoxy alcohols (e.g. TRITON X-100 and X-305 available from Rohm & Haas, Philadelphia, Pa., U.S.A.), p-alkylaryloxypolyglycidols (e.g. SURFACTANT 10G available from Olin Corp., Stamford, Conn., U.S.A.), TWEEN 80 (available from ICI Americas, Inc., Wilmington, Del., U.S.A.), and others known to one skilled in the art.

Useful water-miscible organic solvents include alcohols (e.g. methanol, ethanol, propanol, etc.), N,N-dimethylformamide, dimethyl sulfoxide, acetonitrile, hexamethylenephosphoramide and the like. The particular solvent to be used for a particular composition can be readily determined by routine experimentation.

A dispersion can be prepared in the following general manner. The dye or dye precursor is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, mg surfactant per ml of dispersion. The resulting solution is then mixed with buffer. A suitable mordant, dissolved in buffer at generally from about 0.1 to 20 mg/ml of buffer, is then mixed with the dye or dye precursor dispersion to obtain a composition of this invention. This preparation is generally carried out at room temperature.

In many instances, it is desirable to use the analytical composition at physiological pH (9 or less). The concentration of one or more buffers used to maintain the pH in the dispersion can vary widely, but is generally from about 0.01 to about 1 molar. Representative buffers include phosphates, borates and others reported by Good et al in *Biochemistry*, 5, 467 (1966), and *Anal. Biochem.*, 104, 300 (1980).

The compositions described herein are useful in compositions for assay (i.e. qualitative or quantitative detection) of aqueous and nonaqueous liquids, e.g. biological fluids, manufacturing processes, wastewater, food stuffs, etc. Determinations can be made of various analytes via a single reaction or a sequence of reactions which bring about reduction of the compound and release of the fluorescent moiety. The various analytes include living cells (e.g. bacteria, white blood cells, yeast, fungi, etc.), enzymes (e.g. hydrolases, glucose oxidase, lactate oxidase, creatine kinase, α-glycerophosphate oxidase, lactate dehydrogenase, pyruvate dehydrogenase, glucose-6-phosphate dehydrogenase, alanine aminotransferase, aspartate aminotransferase and other NADH-based, FADH-based or oxidase-based assays which include dehydrogenase or reductase enzymes), biological or chemical reductants other than living cells which will reduce the preferred dye precursor (e.g. ascorbates, cysteine, glutathione, thioredoxin, etc.), metabolizable substances (e.g. glucose, lactic acid, triglycerides, cholesterol, etc.), immunoreactants (e.g. antigens, antibodies, haptens, etc.).

The compositions of this invention are particularly useful in determining living cells in biological samples. Although any biological sample suspected of having living cells therein (e.g. food, tissue, ground water, cooling water, pharmaceutical products, sewage, etc.)

can be analyzed for bacteria, yeast, fungi, etc. by this invention, the invention is particularly useful for bacterial detection in aqueous liquids, such as human and animal fluids (e.g. urine, cerebral spinal fluid, whole blood, blood serum and plasma and the like as well as stool secretions) and suspensions of human or animal tissue. The practice of this invention is particularly important for detection of urinary tract infections in urine (diluted or undiluted).

When determining living cells using this invention, it is preferable for rapid dye release that the living cells interact with an electron transfer agent (identified herein as an ETA). The presence of an ETA may also provide more efficient dye formation for analytical determinations of nonliving analytes. The ETA is a mobile compound which acts as an intermediary between the substance being determined (e.g. living cell) and a reducible dye precursor.

In general, the ETA compounds useful in the practice of this invention have an $E_{\frac{1}{2}}$ in the range of from about $-320$ to about $+400$ mV as measured in aqueous buffer (pH 7) versus the normal hydrogen electrode using a differential pulse polarographic technique with a PAR Potentiostat (Princeton Applied Research, Princeton, N.J.). In general, the potential of the ETA should be more positive than the potential of the analyte to be determined and less positive than the potential of the reducible dye precursor (e.g. a RIND compound). The ETA is generally present at a concentration that is dependent upon the concentration of the analyte, and preferably at a concentration of from about $1 \times 10^{-3}$ molar to about $1 \times 10^{-7}$ molar.

ETA compounds useful in the practice of this invention include phenazine methosulfate, phenazine ethosulfate and similar compounds known to one skilled in the art. Combinations of different ETA compounds can be used if desired.

Preferred ETA compounds useful in the practice of this invention which provide further advantages of low background are those which are the subject of U.S. Ser. No. 699,374 filed by Mura et al on Feb. 7, 1985, the disclosure of which is incorporated herein by reference. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, 2,6-dimethoxy-1,4-benzoquinone, 2-hydroxymethyl-1,4-naphthoquinone and 2-(2-hydroxyethyl)-1,4-naphthoquinone.

The determination of living cells, and particularly of bacterial cells, is often carried out in the presence of a nutrient for those cells although its presence is not essential. Any nutrient medium can be used which contains useful carbon, and optionally nitrogen, sources. Suitable nutrient media having proper components and pH are well known in the art.

The present invention is adaptable to either solution or dry assays. In a solution assay, a solution (or aqueous dispersion) containing a rigid fluorescent dye or precursor thereof, a mordant, and preferably an ETA, can be prepared and contacted, by mixing, with a liquid test sample containing the analyte to be determined. Generally the composition is mixed with the test sample in a suitable container (e.g. test tube, petri dish beaker, cuvette, test device, etc.). The resulting solution (or dispersion) is gently mixed and incubated for a relatively short time (i.e. up to about 30 minutes) at a temperature up to about 40° C., and generally from about 20° to about 40° C. The test sample is then evaluated by measuring the resulting fluorescent dye with suitable detection equipment.

The solution assay can also be carried out by contacting a porous absorbent material, e.g. paper strip, containing the test sample with the composition of this invention. The analyte in the test sample can migrate from the porous material into the composition and initiate the analytical reactions needed for determination. In solution assays, the amount of dye or dye precursor present is at least about 0.001, and preferably from about 0.01 to about 1.0, millimolar. The amount of mordant is at least 0.1, and preferably from about 0.5 to about 10% (based on final weight). Other reagents can be present in amounts readily determined by one skilled in the art.

Alternatively, the method of this invention can be practiced with a dry analytical element. Such an element can be an absorbent carrier material, i.e. a thin sheet or strip of self-supporting absorbent or bibulous material, such as filter paper or strips, which contains the composition of this invention or a dried residue of a dispersion comprising same. Such elements are known in the art as test strips, diagnostic elements, dip sticks, diagnostic agents and the like. The rigid dye or dye precursor and the polymeric mordant must be in the element in a manner that they can interact with each other. This is termed "in association". If they are not in the same area of the element, the dye or dye precursor is capable of migrating to the mordant during the assay.

When employed in dry analytical elements, the composition of this invention can be incorporated into a suitable absorbent carrier material by imbibition or impregnation, or can be coated on a suitable material. Alternatively, it can be added to the element during an assay. Useful carrier materials are insoluble and maintain their structural integrity when exposed to water or physiological fluids such as urine or serum. Useful carrier materials can be prepared from paper, porous particulate structures, cellulose, porous polymeric films, wood, glass fiber, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

A dry assay can be practiced to particular advantage with an analytical element comprising a support having thereon at least one porous spreading zone as the absorbent carrier material. The spreading zone can be prepared from any suitable fibrous or non-fibrous material or mixtures of either or both as described in U.S. Pat. No. 4,292,272 (issued Sept. 29, 1981 to Kitajima et al), or from polymeric compositions (e.g. blush polymers) or particulate materials, with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication No. 57(1982)-101760 (published June 24, 1982). It is desired that the spreading zones be isotropically porous, meaning that the porosity is the same in each direction in the zone as created by interconnected spaces or pores between particles, fibers, polymeric strands, etc.

The dry analytical element of this invention can be a single self-supporting porous spreading zone containing the composition of this invention, but preferably such zone is carried on a suitable non-porous support. Such a support can be any suitable dimensionally stable, and preferably, transparent (i.e. radiation transmissive) film or sheet material which transmits electromagnetic radiation of a wavelength between about 200 and about 900 nm. A support of choice for a particular element should be compatible with fluorescence spectroscopy and inert to chemical reagents and liquid samples used in the assay. Useful support materials include polystyrene, polyesters [e.g. poly(ethylene terephthalate)], polycarbonates, cellulose esters (e.g. cellulose acetate), etc.

The elements can have more than one zone, e.g. a reagent zone, a registration zone, subbing zone, etc. The zones are generally in fluid contact with each other, meaning that fluids, reagents and reaction products can pass between superposed regions of adjacent zones. In particular, if the dye precursor is not in the same zone as the mordant, the element can be designed to allow migration of the released dye to the mordant. Preferably, the zones are separately coated superposed layers, although two or more zones can be in a single layer. Besides the Przybylowicz et al and Pierce et al patents noted above, suitable element formats and components are described also, for example, in U.S. Pat. Nos. 4,042,335 (issued Aug. 16, 1977 to Clément) and 4,144,306 (noted above) and U.S. Pat. No. Re. 30,267 (reissued May 6, 1980 to Bruschi).

In the elements of this invention, the dye precursor, mordant and any other reagents can be in the same or different zones. During the assay, if in different zones, the released dye migrates through the element until it comes into contact with the mordant. The amount of the fluorescent dye or dye precursor can be varied widely, but it is generally present in a coverage of at least about 0.01, and preferably from about 0.05 to about 0.2, $g/m^2$. Other necessary or optional reagents are generally present in the following coverages:

mordant: generally at least about 0.1, and preferably from about 0.5 to about 5, $g/m^2$,
ETA: generally at least about 0.001, and preferably from about 0.01 to about 1, $g/m^2$,
nutrient: generally at least about 0.005, and preferably from about 0.1 to about 2, $g/m^2$ (used only in living cell detection),
buffer (pH≦9): generally at least about 0.1, and preferably from about 0.5 to about 2, $g/m^2$, and
surfactant: generally at least about 0.1, and preferably from about 0.2 to about 5, $g/m^2$.

The element zones can contain a variety of other desirable, but optional, addenda, including activators, binders (generally hydrophilic), anti-oxidants, etc. as is known in the art.

In a preferred embodiment of this invention, an element for determination of microorganisms or cells (e.g. yeast, white blood cells, fungi, bacteria, etc.) in an aqueous liquid contains an electron transfer agent, a nonionic mordant and a reducible dye precursor described above (e.g. a RIND compound). It is desirable that these elements also contain a nutrient for the living cells and a buffer which maintains physiological pH during the assay (e.g. when contacted with a 1–200 μl sample of test liquid). Such an element can be used to detect bacteria, for example, in a urine sample by contacting the sample and element in a suitable manner, and detecting the rigid fluorescent dye released from the dye precursor at the appropriate wavelength. A urine sample may have to be pretreated before testing to eliminate reductive interferents.

In antoher embodiment of this invention, an element for the determination of a nonliving biological or chemical analyte in an aqueous liquid comprises the dye precursor and a mordant as described above, and optionally an ETA, a nonionic surfactant and a buffer which maintains physiological pH during the assay, all of which are described above. Examples of such analytes are described above. The elements may also contain suitable interactive composition comprising suitable reagents which react with the analyte and effect release of the fluorescent dye. The amount of dye detected can be correlated to the amount of analyte present in the liquid sample.

The element of this invention is also useful for determining reductants such as ascorbate (ascorbic acid and equivalent alkali metal salts), cysteine, glutathione, thioredoxin and the like.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and physically contacting it with a sample (e.g. 1–200 μl) of the liquid to be tested so that the sample is mixed with the reagents in the element. Such contact can be accomplished in any suitable manner, e.g. dipping or immersing the element into the smaple or, preferably, by spotting the element by hand or machine with one or more drops of the sample with a suitable dispensing means so that the liquid sample mixes with the reagents within the element.

After sample application, the element is exposed to any conditioning, such as incubation, heating or the like, that may be desirable to quicken or otherwise facilitate obtaining any test result.

Determination of an analyte or living cell is achieved when a fluorescent dye is released which can be detected in a suitable manner using conventional fluorometric apparatus and detection procedures. Determinations can be made at the maximum wavelength or at other wavelengths.

In the examples provided below to illustrate the practice of this invention, the materials used were obtained from the following sources:
ZONYL FSN surfactant from DuPont Co. (Wilmington, Del., U.S.A.),
DAXAD 30 surfactant from W. R. Grace Co. (Lexington, Mass., U.S.A.),
TRITON X-100 surfactant from Rohm and Haas (Philadelphia, Pa.), and
the remainder from Eastman Kodak Company (Rochester, N.Y.) or pepared using known starting materials and techniques.

As used in the context of this disclosure and the claims, I.U. represents the International Unit for enzyme activity defined as one I.U. being the amount of enzyme activity required to catalyze the conversion of 1 μmole of substrate per minute under standard pH and temperature conditions for the enzyme.

Examples 1-3: Fluorescence Enhancement of Phenalenone and benzphenalenone Dyes Using Mordants Compositions were prepared containing each of the fluorescent dyes I, II and III identified above and each of several polymeric mordants. The fluorescence intensity of each composition was compared to the intensity of a Control composition containing the dye alone. The fluorescent scans were made using an excitation maxima of 540 nm and emission maxima of 600 nm for dyes I and II, and an excitation maxima of 540 nm and an emission maxima of 670 nm for dye III.

The compositions were prepared in the following manner:

Compositions Ia, Ib, Ic and Id of Example 1 contained dye I (5.83 μmolar) and poly(styrene-co-N,N,N-trimethyl-N-vinylbenzylammonium chloride)(1.8 mg/ml), poly(N-cyclohexyl-N,N-dimethyl-N-vinylbenzylammonium chloride)(1.8 mg/ml), poly(1-vinyl imidazole-co-3-(2-hydroxyethyl)-1-vinylimidazolium chloride)(1.8 mg/ml) and poly(N-vinylpyrrolidone)(1.8 mg/ml), respectively, in 50 mmolar sodium phosphate buffer (pH 7.5). A Control composition contained dye I (5.83 μmolar) in 50 mmolar sodium phosphate buffer (pH 7.5).

Compositions IIa, IIb, IIc and IId of Example 2 and Control composition II were prepared similarly except dye II was used.

Composition III of Example 3 contained dye III (9.2 μmolar) and poly(styrene-co-N,N,N-trimethyl-N-vinylbenzylammonium chloride)(1.8 mg/ml) in 50 mmolar sodium bicarbonate buffer (pH 10). Control composition III was prepared with dye III only in buffer.

Table II below lists the increase in fluorescence intensity for the compositions of this invention over the intensities of the respective Control compositions.

TABLE II

| Composition | Intensity Increase |
| --- | --- |
| Ia | 40% |
| Ib | 35% |
| Ic | 4% |
| Id | 19% |
| IIa | 20% |
| IIb | 52% |
| IIc | 64% |
| IId | 51% |
| III | 76% |

Example 4: Fluorescence Enhancement in a Determination of an Esterase Enzyme

This example demonstrates the use of the present invention to determine an analyte, diacetinase, with the composition of the present invention. It also shows the improved fluorescence intensity obtained with that composition.

The fluorescent dye precursor (4 mg) having the following structure and prepared according to the procedure described in U.S. Ser. No. 824,752 of Babb et al entitled HYDROLYZABLE FLUORESCENT SUBSTRATES AND ANALYTICAL DETERMINATIONS USING SAME, noted above, was dissolved in N,N-dimethylformamide (250 μl) containing 0.1% sulfuric acid. Some of this solution (75 μl) was mixed with TRITON X-100 surfactant (600 μl) and sodium phosphate buffer (30 ml, 50 mmolar, pH 7) to form Solution A, and kept in the dark.

A Control composition was prepared with 3 ml of Solution A and 10 μl of diacetinase (0.2 I.U./ml of water). A composition of this invention was prepared from 3 ml of Solution A, 10 μl of diacetinase and 40 μl of poly(N-cyclohexyl-N,N-dimethyl-N-vinylbenzylammonium chloride)(15 mg/ml of buffer).

Fluorescent scans were run at 25° C. for 40 minutes with readings taken at 10 minute intervals using a commercially available Perkin-Elmer fluorometer. The excitation maxima was 540 nm and the emission maxima was 598 nm.

Figure 1:
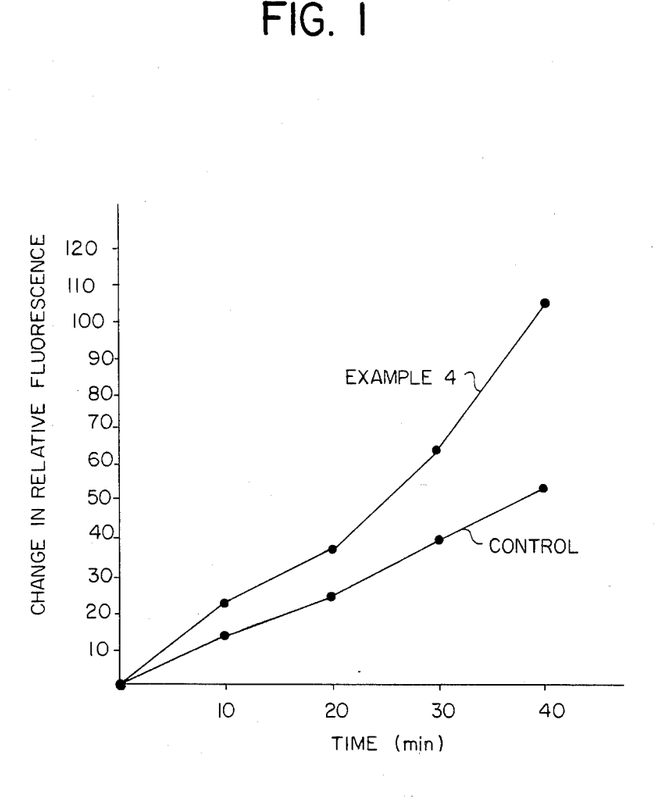

The Figure shows the change in relative fluorescence vs. time for both compositions. It is clear that the present invention provides significantly improved fluorescence compared to the Control composition where the mordant was absent.

Example 5: Staining of White Blood Cells Using a Composition of this Invention

This example demonstrates the usefulness of the present invention to stain white blood cells.

Human blood (5 ml) was collected in sterile vacutainer tubes containing 1.5 ml acid citrate dextrose as an anticoagulant, and 1.5-2 ml of 6 g% dextran (molecular weight 60,000-90,000, available from Sigma Chemical Co. St. Louis, Mo., U.S.A.) was added to each tube. The tubes were mixed by inversion and allowed to settle at 25° C. for 1.5-2 hours. The plasma containing the buffy coat was removed and transferred to a 7 ml plastic tissue culture tube, centrifuged at 1000 RPM for 10 minutes and decanted. The cells were washed with phosphate buffer saline solution, (PBS) (8.7 sodium chloride in 0.05 molar potassium phosphate buffer, pH 7.3) and 10 ml of lysing solution [155 mmolar ammonium chloride, 10 mmolar potassium bicarbonate and 0.008 mmolar (ethylenedinitrilo)tetraacetic acid, disodium salt, pH 7.2] was added and the resulting solution was allowed to set at 25° C. for 5 minutes. The resulting lysed cell mixture was centrifuged, decanted and the pellet was washed with PBS solution and resuspended in 0.5 ml PBS solution.

The white blood cells were treated with Dye Compound I identified above (23 mg) in 700 μl N,N-dimethylformamide and 35 ml of 0.1 molar potassium phosphate buffer (pH 7) (final dye concentration of $1.2 \times 10^{-4}$ molar) and 0.18 g% (final concentration) of the mordant poly(styrene-co-N,N,N-trimethyl-N-vinylbenzylammonium chloride) for 1-3 hours. The stained cells were then dried and fixed of a glass slide with methanol and washed three times with water to remove excess dye.

The stained cell preparations were examined with a Zeiss fluorescence microscope against a dark background (excitation at 510–560 nm and emission at 590 nm). Bright pink fluorescence of the white blood cells was observed

Example 6: Determination of *E. coli* With RIND I and a Mordant in a Dry Element This example is taken from U.S. Ser. No. 824,757 of Babb et al (Example 11), noted above. It shows the use of the present invention to determine a microorganism, *E. coli*. A dry element having the following format was used in this example.

| | | |
|---|---|---|
| Spreading/ Reagent Layer | Poly(vinyltoluene-co-p-t-butylstyrene-co-methacrylic acid) Beads | 100–150 g/m² |
| | Poly(n-butyl acrylate-co-styrene-co-2-acrylamido-2-methylpropane sulfonic acid, sodium salt) | 2–6 g/m² |
| | TRITON X-100 surfactant | 2–5 g/m² |
| | Glucose | 0.1–0.5 g/m² |
| | RIND I (of Table I above) | 0.1–0.5 g/m² |
| | 2,3,5-Trimethyl-1,4-benzoquinone | 0.8–4 g/m² |
| Reflection Layer | Gelatin (hardened) | 1–10 g/m² |
| | Titanium dioxide | 0.5–5.0 g/m² |
| | ZONYL FSN surfactant | 0.1–0.5 g/m² |
| | DAXAD 30 surfactant | 0.02–0.04 g/m² |
| Mordant/ Registration Layer | Gelatin (hardened) | 1–10 g/m² |
| | Poly(styrene-co-N—benzyl-N,N—dimethyl-N—(p-vinylbenzyl)ammonium chloride-co-divinylbenzene) mordant | 0.5–5.0 g/m² |
| | ZONYL FSN surfactant | 0.1–0.5 g/m² |
| | Poly(ethylene terephthalate) Support | |

To evaluate this element, solution of varying *E. coli* cell concentrations in potassium phosphate buffer (pH 7.5) and a Control containing only buffer were prepared. These solutions were then spotted onto the element using 10 μl drops, and the element was incubated at 37° C. for up to 60 minutes. The fluorescence was measured in a modified, commercially available fluorometer (excitation, 540 nm, emission, 620 nm) after 3 minutes and at 60 minutes. The results, listed in Table III below, are the differences (Δ) in relative fluorescence at 3 and 60 minutes. They indicate that approximately $10^7$ cells/ml can be detected using this element.

TABLE III

| E. coli (Cells/ml) | Δ Relative Fluorescence (57 Min., 37° C.) | Standard Deviation | CV (%)* |
|---|---|---|---|
| $1.0 \times 10^7$ | 0.272 | 0.007 | 2.6 |
| $4.1 \times 10^6$ | 0.249 | 0.007 | 2.8 |
| 0 | 0.221 | 0.010 | 4.5 |

The invention has been described in detail with particular reference to preferred embodiments thereof, but it will be understood that variations and modifications can be effected within the spirit and scope of the invention.

I claim:

1. An analytical dye composition comprising a rigid phenalenone, benzphenalenone or 4-oxo-4H-benz-[d,e]anthracene fluorescent dye or a hydrolyzable or reducible precursor thereof which releases a rigid fluorescent dye upon hydrolysis or reduction, respectively, of said precursor and a cationic or nonionic polymeric mordant.

2. The composition of claim 1 wherein said fluorescent dye is a phenalenone or benzphenalenone dye.

3. The composition of claim 1 comprising a reducible fluorescent dye precursor of the structure CAR$\pm$(R$^1$)$_n$ wherein CAR— is an aromatic or quinone nucleus having one or more hydrogen atoms removed to provide one or more valences through which R$^1$ is attached to CAR—, R$^1$ comprises a phenalenone or benzphenalenone moiety derived from wherein R is hydroxy or mercapto, said moiety being attached to CAR— through an oxy or thio linkage obtained by removal of hydrogen from R, and n is 1 or 2, provided that when R$^1$ is replaced with H, CA-R—(H)$_n$ has an E$_{\frac{1}{2}}$ of either at least about +100 mV when measured in water.

4. The composition of claim 3 wherein said dye precursor has the structure CAR—R$^1$, wherein CAR— is R$^1$ is R$^2$ and R$^4$ are independently hydrogen, alkyl, aryl or an electron withdrawing group, R$^3$ is R$^1$, hydrogen, alkyl, aryl or an electron withdrawing group, or R$^3$ and R$^4$, taken together, represent the atoms necessary to complete a fused carbocyclic ring, R$^5$ is alkylene or 1 or 2 carbon atoms,

R$^6$ is methyl,

Q is carbonyl or thiocarbonyl,

FRAG is said phenalenone or benzphenalenone moiety attached to Q through said oxy or thio linkage, and m is 0 or 1.

5. The composition of claim 4 wherein FRAG is

6. The composition of claim 1 comprising a cationic polymeric mordant.

7. The composition of claim 1 buffered at a pH of 9 or less.

8. A composition for the determination of a living organism, said composition comprising
an electron transfer agent,
a cationic or nonionic mordant, and
a reducible fluorescent dye precursor of the structure CAR—$(R^1)_n$ wherein CAR— is an aromatic or quinone nucleus having one or more hydrogen atoms removed to provide one or more valences through which $R^1$ is attached to CAR—,
$R^1$ is wherein $R^5$ is alkylene of 1 or 2 carbon atoms, $R^6$ is methyl, Q is carbonyl or thiocarbonyl and FRAG is a phenalenone or benzphenalenone moiety derived from wherein R is hydroxy or mercapto, said moiety being attached to Q through an oxy or thio linkage obtained by removal of hydrogen from R, and n is 1 or 2,
provided said precursor is capable of being reduced at physiological pH.

9. The composition of claim 8 wherein said dye precursor has the structure CAR—$R^1$, wherein CAR— is $R^2$ and $R^4$ are indepenndently hydrogen, alkyl, aryl or an electron withdrawing group,
$R^3$ is $R^1$, hydrogen, alkyl, aryl or an electron withdrawing group, or $R^3$ and $R^4$, taken together, represent the atoms necessary to complete a fused carbocyclic ring, and
m is 0 or 1,
provided that when $R^1$ is replaced with H, CAR—H has an $E_{\frac{1}{2}}$ of at least about +100 mV when measured in water.

10. The composition of claim 8 further comprising a surfactant.

11. A dry analytical element for the determination of an analyte comprising an absorbent carrier material, and containing, in association, a rigid phenalenone, benzphenalenone or 4-oxo-4H-benz-[d,e]-anthracene fluorescent dye or a hydrolyzable or reducible precursor thereof which releases a rigid fluorescent dye upon hydrolysis or reduction, respectively, of said precursor and a cationic or nonionic polymeric mordant.

12. The element of claim 11 wherein said fluorescent dye precursor is a reducible compound of the structure CAR—$(R^1)_n$ wherein CAR— is an aromatic or quinone nucleus, having one or more hydrogen atoms removed to provide one or more valences through which $R^1$ is attached to CAR—,
$R^1$ is wherein $R^5$ is alkylene of 1 or 2 carbon atoms, $R^6$ is methyl, Q is carbonyl or thiocarbonyl and FRAG is a phenalenone or benzphenalenone moiety derived from wherein R is hydroxy or mercapto, said moiety being attached to Q through an oxy or thio linkage obtained by removal of hydrogen from R, and n is 1 or 2.

13. The element of claim 12 wherein said dye precursor has the structure CAR—$R^1$, wherein CAR— is $R^2$ and $R^4$ are independently hydrogen, alkyl, aryl or an electron withdrawing group,
$R^3$ is $R^1$, hydrogen, alkyl, aryl or an electron withdrawing group, or $R^3$ and $R^4$, taken together, represent the atoms necessary to complete a fused carbocyclic ring, and m is 0 or 1, provided that when $R^1$ is replaced with H, CAR—H has an $E_{\frac{1}{2}}$ of at least about +100 mV when measured in water.

14. The element of claim 13 wherein FRAG is a phenalenone moiety.

15. The element of claim 11 further comprising an interactive composition for said analyte.

16. The element of claim 11 further comprising an electron transfer agent.

17. The element of claim 11 further comprising a support carrying said absorbent carrier material.

18. A method for the determination of an analyte, said method comprising the steps of:

A. contacting a sample of a liquid suspected of containing an analyte with a phenalenone, benzphenalenone or 4-oxo-4H-benz-[d,e]anthracene hydrolyzable or reducible fluorescent dye precursor which releases a rigid fluorescent dye upon hydrolysis or reduction, respectively, of said precursor in the presence of said analyte, and a cationic or nonionic polymeric mordant, and

B. determining said dye released upon hydrolysis or reduction, respectively, or said precursor as a result of the presence of said analyte.

19. The method of claim 18 wherein said fluorescent dye precursor is a reducible compound of the structure CAR$+R^1)_n$ wherein CAR— is an aromatic or quinone nucleus having one or more hydrogen atoms removed to provide one or more valences through which $R^1$ is attached to CAR—, $R^1$ is wherein $R^5$ is alkylene of 1 or 2 carbon atoms, $R^6$ is methyl, Q is carbonyl or thiocarbonyl and FRAG is a phenalenone or benzphenalenone moiety derived from wherein R is hydroxy or mercapto, said moiety being attached to Q through an oxy or thio linkage obtained by removal of hydrogen from R, and n is 1 or 2.

20. The method of claim 19 wherein said dye precursor has the structure CAR—$R^1$, wherein CAR— is $R^2$ and $R^4$ are independently hydrogen, alkyl, aryl or an electron withdrawing group, $R^3$ is $R^1$, hydrogen, alkyl, aryl or an electron withdrawing group, or $R^3$ and $R^4$, taken together, represent the atoms necessary to complete a fused carbocyclic ring, and m is 0 or 1, provided that when $R^1$ is replaced with H, CAR—H has an $E_{\frac{1}{2}}$ of at least about +100 mV when measured in water.

21. The method of claim 18 for the determination of a living organism.

22. The method of claim 18 wherein said contacting is carried out in the presence of an electron transfer agent.

23. The method of claim 18 for the determination of a nonliving substance in the presence of an interactive composition for said analyte.

24. A method for distinguishing cells comprising contacting a biological sample containing cells with a composition comprising a rigid phenalenone, benzphenalenone or 4-oxo-4H-benz[d,e]anthracene fluorescent dye or a hydrolyzable or reducible precursor thereof which releases a rigid fluorescent dye upon hydrolysis or reduction, respectively, of said precursor, and a cationic or nonionic polymeric mordant.

* * * * *

UNITED STATES PATENT AND TRADEMARK OFFICE
CERTIFICATE OF CORRECTION

PATENT NO. : 4,803,160
DATED : February 7, 1989
INVENTOR(S) : Annie L. Wu It is certified that error appears in the above-identified patent and that said Letters Patent is hereby corrected as shown below Column 20, line 16;
Column 21, line 39;
Column 22, line 38; and
Column 24, linl 1, the part of the formula reading should read Signed and Sealed this Sixth Day of March, 1990

Attest:

JEFFREY M. SAMUELS

Attesting Officer

Acting Commissioner of Patents and Trademarks